(12) United States Patent
Prinderre (10) Patent No.: US 10,034,883 B2
(45) Date of Patent: Jul. 31, 2018

(54) MESOPOROUS DOSAGE FORMS FOR POORLY SOLUBLE DRUGS

(71) Applicant: SIEGFRIED AG, Zofingen (CH)

(72) Inventor: Pascal Prinderre, Muespach (FR)

(73) Assignee: SIEGFRIED AG, Zofingen (CH)

( * ) Notice: Subject to any disclaimer, the term of this patent is extended or adjusted under 35 U.S.C. 154(b) by 0 days.

(21) Appl. No.: 15/034,055

(22) PCT Filed: Nov. 6, 2014

(86) PCT No.: PCT/EP2014/073886
§ 371 (c)(1),
(2) Date: May 3, 2016

(87) PCT Pub. No.: WO2015/067682
PCT Pub. Date: May 14, 2015

(65) Prior Publication Data
US 2016/0263123 A1    Sep. 15, 2016

(30) Foreign Application Priority Data

Nov. 7, 2013 (EP) .................................. 13005247

(51) Int. Cl.
 *A61K 31/5377*  (2006.01)
 *A61K 9/14*  (2006.01)
 *A61K 9/16*  (2006.01)
 *A61K 31/192*  (2006.01)

(52) U.S. Cl.
CPC .......... *A61K 31/5377* (2013.01); *A61K 9/143* (2013.01); *A61K 9/1611* (2013.01); *A61K 31/192* (2013.01)

(58) Field of Classification Search
None
See application file for complete search history.

(56) References Cited

FOREIGN PATENT DOCUMENTS

| EP | 2279728 A1 | 2/2011 | |
| WO | 2011054046 A1 | 5/2011 | |
| WO | WO 2012035074 A1 * | 3/2012 | ............. A61K 9/143 |

OTHER PUBLICATIONS

European Medicines Agency: CHMP Assessment Report for Xarelto, 2008, pp. 1-56.*
Shi, Zuetao et al., "Novel Mesoporous Silica-Based Antibiotic Releasing Scaffold for Bone Repair," ScienceDirect, Acta Biomaterialia (2009) vol. 5, pp. 1697-1707.
Zhao, Dongyuan et al., "Contiuous Mesoporous Silica Films with Highly Ordered Large Pore Structures," Advanced Materials, (1998) vol. 6156, pp. 1380-1385 (XP-000785447).
International Search Report and Written Opinion for PCT/EP2014/073886 dated Jan. 7, 2015.
Extended European Search Report for EP 13005247.5 dated May 8, 2014.

* cited by examiner

*Primary Examiner* — Jessica Worsham
(74) *Attorney, Agent, or Firm* — Hunton Andrews Kurth LLP (57) ABSTRACT

The present invention is directed to a new pharmaceutical dosage form comprising mesoporous particles loaded with a poorly soluble active pharmaceutical ingredient, the particles being at least partially, preferably homogeneously, covered with a polymer solid dispersion.

12 Claims, 3 Drawing Sheets

MESOPOROUS DOSAGE FORMS FOR POORLY SOLUBLE DRUGS

FIELD OF THE INVENTION

The present invention relates to an improved drug delivery system for poorly soluble drugs. More particularly, the present invention provides new mesoporous material based dosage forms which can improve the dissolution and bioavailability of the poorly soluble drugs. The invention is further related to the corresponding uses and processes. A specific aspect of the present invention is directed to a new dosage form for rivaroxaban.

BACKGROUND OF THE INVENTION

Drug lipophilicity represents a major concern in the development of efficient oral drug delivery and affects a substantial number of new drug candidates. Whereas several technologies are now available to improve the dissolution of lipophilic drugs (e.g. use of surfactants, prodrugs, cyclodextrin inclusions, lipid based formulations, microemulsions, liposomes) these methods are usually complex to perform. Therefore, there is still a need for improved and economical dosage forms having appropriate biopharmaceutical properties.

Nanotechnologies have become an important aspect in the development of improved drug delivery systems. Besides the nanosizing of the active ingredient itself, formulators have also considered the use of nanosized excipients.

Mesoporous materials have pores within their structures which can be loaded with active ingredients. Mesoporous materials are particularly suitable drug delivery carriers for poorly soluble drugs. Once the drug is loaded inside the pores of the mesoporous material, it is believed that the drug maintains in an amorphous or molecularly dispersed state due to a lack of space to crystallize. The drug can be loaded inside of the mesoporous carrier and/or mesoporous matrix and released for dissolution in an aqueous environment.

Porous silica materials have already been disclosed in the prior art. Mesoporous silicas, such as the MCM family, were materials prepared first by the Mobil Oil Company. Several other methods have been developed leading to a great variety of materials having e.g. different pore shapes and size distributions. Examples of such materials are the SBA-15 or 157 MSU products. These materials are for example disclosed in the review of Carrillo et al. "Well ordered mesoporous interconnected silica spheres prepared using extremely low surfactant concentrations", Mater. Chem. Phys. 129 (2011) 261-269. However, these materials are difficult to formulate since they exhibit poor flowability and compression properties.

The article of Vialpando et al., J. of Pharm. Sc. (2013) discloses a comparison between the agglomerations of ordered and non-ordered mesoporous silica materials made by steam and melt granulations. According to Vialpando, the active ingredient on the surface of the particles remains in a crystallized form and does not therefore allow achieving an improved dissolution.

However, the properties of the cited prior art materials are not fully satisfying for poorly soluble drugs. Particularly, it appears that the loading capability of these carriers remains limited and that the dissolution of the active ingredient can further be increased.

SUMMARY OF THE INVENTION

It is an object of the present invention to provide improved pharmaceutical dosage forms for poorly soluble drugs. Furthermore, it is an object of the invention to provide pharmaceutical dosage forms that display an increased solubility (supersaturation) of an active pharmaceutical ingredient in the pharmaceutical dosage form, particularly in a pharmaceutical dosage form comprising particles of a mesoporous material. These objects are solved by the subject-matter of the independent claims. Preferred embodiments are indicated in the dependent claims.

A first aspect of the invention is directed to a pharmaceutical dosage form comprising particles of a mesoporous material loaded with a poorly soluble active pharmaceutical ingredient, wherein the external surfaces of the mesoporous particles are at least partially covered with a polymer solid dispersion of said active pharmaceutical ingredient.

According to another embodiment, the polymer solid dispersion of the poorly soluble active ingredient is an amorphous solid dispersion or a solid solution.

According to another embodiment, the external surface of the particles of the mesoporous material is covered, e.g. coated, with the solid dispersion.

According to another embodiment, the mesoporous material is a silica based material, preferably an ordered or a non-ordered (disordered) silica or a mixture thereof. According to certain embodiments, the mesoporous material is a non-ordered silica. According to certain embodiments, the mesoporous material is an ordered silica.

According to another embodiment, the mesoporous material has a pore size in the range of 2 to 50 nm, preferably in the range of 2 to 20 nm, more preferably in the range of 3 to 15 nm, even more preferably in the range of 3 to 12 nm, and most preferably in the range of 3 to 10 nm.

According to another embodiment, the polymer for the solid dispersion may be selected from cellulose derivatives, polyacrylates, polyvinyl derivatives, polyalkylene oxides, polyamino saccharides and mixtures thereof. A derivative in this regard, as well as within the specification, thereby relates to a compound that is derived from the original compound, e.g. in case of a cellulose derivative from cellulose, by any derivatization reaction, thus leading to a product with similar chemical structure.

According to another embodiment, the poorly soluble drug may be selected from BCS (Biopharmaceutical Classification System) Class II and IV drugs, optionally as described in e.g. Wu et al. "Predicting Drug Disposition via Application of BCS: Transport/Absorption/Elimination Interplay and Development of a Biopharmaceutics Drug Disposition Classification System"; Pharm. Res., Vol. 22, No. 1, January 2005.

According to another embodiment, said poorly soluble drug/poorly soluble active pharmaceutical ingredient may be selected from the group comprising antihypertensives, antianxiety agents, anticardiovascular disorder agents, anticoagulants, antiplatelets, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, tyrosine kinase inhibitors agents, and mixtures thereof.

Preferably, the poorly soluble drug/poorly soluble active pharmaceutical ingredient may be selected from the group comprising antithrombotic, antiplatelets, anticoagulants, such as vorapaxar, rivaroxaban, anti-fungals, such as intraconazole, fluoconazole, terconazole, ketoconazole, griseofulvin, and griseoverdin, anti-infectives such as sulfasalazine, anti-malaria drugs (e.g. atovaquone), immune system modulators (e.g. cyclosporin), cardiovascular drugs (e.g. digoxin and spironolactone), ibuprofen (analgesic), ritonavir, nevirapine, lopinavir (antiviral), clofazinine (leprostatic), diloxanide furoate (anti-amebic), glibenclamide (anti-diabetes), nifedipine (anti-anginal), spironolactone (diuretic), sterols or steroids such as danazol, carbamazepine, anti-virals such as acyclovir, antibiotics such as amoxicillin, tetracycline, or metronidazole, acid suppressants (H2 blockers including cimetidine, ranitidine, famotidine, and nizatidine, proton pump inhibitors including omeprazole, lansoprazole, rabeprazole, esomeprazole, and pantoprazole), mucolytic agents(megaldrate), acetazolamide, furosemide, tobramycin, cefuroxime, allopurinol, dapsone, doxycycline, paracetamol, nalidixic acid, clorothiazide, tobramycin, cyclosporin, tacrolimus, andpaclitaxel, prostaglandines, e.g. prostaglandine E2, prostaglandine F2 and prostaglandine E1, cytotoxics, e.g. paclitaxel, doxorubicin, daunorubicin, epirubicin, idarubicin, zorubicin, mitoxantrone, amsacrine, vinblastine, vincristine, vindesine, dactiomycine, bleomycine, metallocenes, e.g. titanium metallocene dichloride, lipid-drug conjugates, e.g. diminazene stearate and diminazene oleate, anti-infectives such as clindamycin, antiparasitic drugs, e.g chloroquine, mefloquine, primaquine, vancomycin, vecuronium, pentamidine, metronidazole, nimorazole, tinidazole, atovaquone, buparvaquone, nifurtimoxe, anti-inflammatory drugs, e.g. methotrexate, azathioprine, androgen receptor antagonists, e.g. enzalutamide, drugs used for the treatment of insomnia, e.g. suvorexant, their pharmaceutically acceptable salts, hydrates and mixtures thereof.

Preferably, the poorly soluble drug is rivaroxaban, its pharmaceutically acceptable salts, hydrates or mixtures thereof.

According to another embodiment, the poorly soluble drug represents between 5 and 60% wt of the total weight of the mesoporous material and active ingredient, preferably between 10 and 50% wt, and more preferably between 20 and 40% wt.

According to another embodiment, the weight ratio between the active ingredient and the polymer is preferably between 1:10 to 2:1, more preferably in the range of 1:6 to 1.5:1 and most preferably in the range of 2:5 to 1:1.

According to another embodiment, the pharmaceutical dosage forms comprise less than 5% wt of the poorly soluble drug in a crystalline form, preferably less than 1% wt. More preferably, the pharmaceutical dosage forms are free of crystalline forms of the poorly soluble drug/poorly soluble active pharmaceutical ingredient. In certain aspects, the poorly soluble active pharmaceutical ingredient is in an amorphous or molecularly dispersed state.

According to another embodiment, the pharmaceutical dosage forms may be in the form of tablets or capsules.

Another aspect of the present invention is directed to the pharmaceutical dosage forms according to the invention for the prophylaxis and/or treatment of thromboembolic disorders, wherein the poorly soluble drug is rivaroxaban.

According to another embodiment, the poorly soluble drug is rivaroxaban in an amount of 10, 15 or 20 mg, preferably 20 mg.

According to another embodiment, the pharmaceutical dosage form is prepared by hot melt extrusion or by hot melt granulation.

Another aspect of the present invention is directed to the process of a preparation of a pharmaceutical dosage form of a poorly soluble active pharmaceutical ingredient which comprises loading the poorly soluble active pharmaceutical ingredient onto and into a mesoporous material, and dispersing the mesoporous material loaded with the active pharmaceutical ingredient with at least one polymer to prepare a solid dispersion of at least one polymer with a mesoporous material loaded with said active pharmaceutical ingredient.

According to another embodiment, the pharmaceutical dosage form is prepared by hot melt granulation of the at least one polymer and the mesoporous material loaded with the active pharmaceutical ingredient.

According to another embodiment, the particles are at least partially covered, e.g. coated, with the solid dispersion, preferably entirely covered, e.g. coated.

According to another embodiment, the solid dispersion is prepared by hot melt extrusion of the at least one polymer and the mesoporous material loaded with the active pharmaceutical ingredient.

According to another embodiment, the weight ratio between the polymer and the mesoporous material is preferably between 1:3 to 3:1, more preferably in the range of 1:2 to 2:1 and most preferably in the range of 2:3 to 3:2.

According to another embodiment, fillers, like talcum, may further be added to the composition prior to the preparation of the solid dispersion.

According to another embodiment, the solid dispersion may further be milled.

According to another embodiment, the product may further be compressed or formulated in a pharmaceutical dosage form, e.g. in a tablet or a capsule, preferably a tablet.

Another aspect of the present invention is directed to the use of a polymer solid dispersion on a mesoporous material loaded with rivaroxaban or a pharmaceutically acceptable salt or hydrate thereof to improve the bioavailability of rivaroxaban.

A further aspect is directed to a pharmaceutical dosage form prepared by the process according to the invention.

DETAILED DESCRIPTION OF THE INVENTION

All ranges disclosed herein are to be considered to be supplemented by the term "about", unless clearly defined to the contrary or otherwise clear from the context.

All numbers or percentages relating to amounts of a substance within this application are given in wt. %, unless clearly defined to the contrary or otherwise clear from the context.

It is an object of the present invention to provide pharmaceutical dosage forms for poorly soluble active ingredients, particularly active pharmaceutical ingredients, which improve the bioavailability of said active ingredients.

The poorly soluble drug/poorly soluble active pharmaceutical ingredient according to the present invention may be selected from BCS (Biopharmaceutical Classification System of the Food and Drug Administration; "FDA") Class II and IV drugs. The solubility classification of a drug in the BCS is based on the highest dose strength in an IR (immediate release) product. A drug substance is considered highly soluble when the highest strength is soluble in 250 ml or less of aqueous media over the pH range of 1.0-7.5 at 37° C.; otherwise, the drug substance is considered poorly soluble, as e.g. defined in Wu et al. "Predicting Drug Disposition via Application of BCS: Transport/Absorption/Elimination Interplay and Development of a Biopharmaceutics Drug Disposition Classification System"; Pharm. Res., Vol. 22, No. 1, January 2005, which is incorporated with regard to the definition of solubility. According to certain aspects, a poor solubility is considered when the highest strength of the drug substance, i.e. an active pharmaceutical ingredient, is not soluble in 250 ml or less of aqueous media over the pH range of 1.0-7.5 at 37° C. The highest strength of the drug substance thereby depends on the drug substance and can vary, depending on the drug substance. The highest strengths of drug substances are easily available for known drugs, particularly the ones described with regard to this invention, from literature, e.g. the above article of Wu et al. and articles cited therein.

According to another embodiment, said poorly soluble drug may be selected from the group comprising antihypertensives, antianxiety agents, anticardiovascular disorder agents, antiplatelets, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, antidepressants, antiviral agents, tyrosine kinase inhibitors agents, and mixtures thereof. Preferably, the poorly soluble drugs are selected from the group comprising antithrombotic, antiplatelets, anticoagulants, such as vorapaxar, rivaroxaban, anti-fungals, such as intraconazole, fluoconazole, terconazole, ketoconazole, griseofulvin, and griseoverdin, anti-infectives such as sulfasalazine, anti-malaria drugs (e.g. atovaquone), immune system modulators (e.g. cyclosporin), cardiovascular drugs (e.g. digoxin and spironolactone), ibuprofen (analgesic), ritonavir, nevirapine, lopinavir (antiviral), clofazinine (leprostatic), diloxanide furoate (anti-amebic), glibenclamide (anti-diabetes), nifedipine (anti-anginal), spironolactone (diuretic), sterols or steroids such as danazol, carbamazepine, anti-virals such as acyclovir, antibiotics such as amoxicillin, tetracycline, or metronidazole, acid suppressants (H2 blockers including cimetidine, ranitidine, famotidine, and nizatidine, proton pump inhibitors including omeprazole, lansoprazole, rabeprazole, esomeprazole, and pantoprazole), mucolytic agents (megaldrate), acetazolamide, furosemide, tobramycin, cefuroxime, allopurinol, dapsone, doxycycline, paracetamol, nalidixic acid, clorothiazide, tobramycin, cyclosporin, tacrolimus, andpaclitaxel, prostaglandines, e.g. prostaglandine E2, prostaglandine F2 and prostaglandine E1, cytotoxics, e.g. paclitaxel, doxorubicin, daunorubicin, epirubicin, idarubicin, zorubicin, mitoxantrone, amsacrine, vinblastine, vincristine, vindesine, dactiomycine, bleomycine, metallocenes, e.g. titanium metallocene dichloride, lipid-drug conjugates, e.g. diminazene stearate and diminazene oleate, anti-infectives such as clindamycin, antiparasitic drugs, e.g chloroquine, mefloquine, primaquine, vancomycin, vecuronium, pentamidine, metronidazole, nimorazole, tinidazole, atovaquone, buparvaquone, nifurtimoxe, anti-inflammatory drugs, e.g. methotrexate, azathioprine, androgen receptor antagonists, e.g. enzalutamide, drugs used for the treatment of insomnia, e.g. suvorexant, their pharmaceutically acceptable salts, hydrates and mixtures thereof.

Preferably, the poorly soluble drug is rivaroxaban, its pharmaceutically acceptable salts, hydrates or mixtures thereof.

The term "active ingredient", respectively "active pharmaceutical ingredient" within the present invention is directed either to one or a mixture of several active ingredients, respective active pharmaceutical ingredients. The present pharmaceutical dosage forms comprise active ingredients, particularly active pharmaceutical ingredients.

The pharmaceutical dosage forms according to the present invention are particularly suitable for the delivery of rivaroxaban. Rivaroxaban belongs to a class of non-peptidic factor Xa inhibitors which have an oxazolidinone core structure. Rivaroxaban was originally disclosed in the patent application WO 2001/047919 for the oral prophylaxis and treatment of thromboembolic disorders. It shows a very poor solubility in water, physiological media and most solvents. It thus requires complex formulation efforts to provide an efficient administration of rivaroxaban to the patient.

A new dosage form has now been surprisingly found which exhibits improved dissolution profiles. Regarding particularly rivaroxaban, the new dosage form according to the present invention shows a substantially better dissolution profile of rivaroxaban than the currently marketed product Xarelto® 20 mg.

The pharmaceutical dosage forms according to the present invention comprise mesoporous particles which particles are loaded with a poorly soluble active pharmaceutical ingredient and are at least partially, preferably homogeneously, covered, e.g. coated, with a polymer solid dispersion.

In reference to the IUPAC standards, a mesoporous material is defined as of a material having pore diameters between 2 and 50 nm in comparison to microporous materials which pore diameters are less than 2 nm and macroporous materials which pore diameters are greater than 50 nm. A similar definition can be found in e.g. J. Rouquerol et al. "Recommendations for the characterization of porous solids (Technical Report)", Pure & Appl. Chem. Vol. 66 (8): 1739-1758 (1994), which is incorporated herein with regard to mesoporous material.

The term "mesoporous material" as used herein means any material having fine pores with the above pore diameters, and is not particularly limited. It can comprise according to certain aspects of the invention silica or alumina based materials or other materials, e.g. silica ($SiO_2$), e.g. Syloid® like Syloid® AL-1FP or Syloid® 72FP, alumina, magnesium alumino-metasilicates like $Al_2O_3 \cdot MgO \cdot 1.7SiO_2 \cdot xH_2O$, e.g. Neusilin® US2, further mixed inorganic oxides, CaCO3, clay, or further materials as also mentioned in WO 2012/072580 and WO2014/078435, e.g. SB A-15 mesoporous silica, MCM-41, COK-12 which are incorporated herein with regard to mesoporous materials. According to the present invention, the silica based mesoporous materials are the most advantageous materials. Suitable materials are e.g. the silica based materials available from the companies Nanologica, Formac, Merck Millipore, Fuji or Grace.

Typically, mesoporous material may be either non-ordered or ordered in mesostructures. In the latter situation, the voids between the atoms are arranged in an ordered manner depending on the conditions of the preparation process.

Both types of mesoporous materials as well as their mixtures are covered by the present invention. According to certain aspects, the mesoporous material is ordered. According to certain aspects, the mesoporous material is non-ordered.

In the pharmaceutical forms of the present invention, the mesoporous particles are loaded with the active ingredient(s) and at least partially covered, e.g. coated, with a polymer solid dispersion. This means that at least part of the external surface of the particles is covered with the polymer solid dispersion. This polymer solid dispersion, hereinafter sometimes also referred to as a solid dispersion, is a dispersion of the active pharmaceutical ingredient in at least one polymer wherein the active pharmaceutical ingredient is in an amorphous or molecularly dispersed state. The inventors found that during loading of the mesoporous material with the active pharmaceutical ingredient the pores of the mesoporous material are loaded with the active pharmaceutical ingredient and furthermore the active pharmaceutical ingredient can be loaded, on the external surfaces, i.e. not the surfaces of the pores, of the mesoporous material. When treating such mesoporous material loaded with the active pharmaceutical ingredient into and onto the mesoporous material with at least one polymer, particularly according to the process of the present invention, the active pharmaceutical ingredient on the external surfaces of the mesoporous material is dispersed in the at least one polymer. Preferably, a substantial part of the external surface of the particles, more preferably at least 90%, and even more preferably at least 99% of the external surface of the particles is covered with the solid dispersion. Most preferably, the particles are completely covered, e.g. coated, with the solid dispersion. A complete coating is achieved when the mesoporous particles are e.g. hot melt extruded with one or several suitable polymers. Particularly, the polymer substantially does not enter the pores of the mesoporous material, in particular using the process of the present invention. According to certain aspects of the invention, the polymer does not enter the pores of the mesoporous material.

The loading of the active ingredient into and onto the mesoporous material can be performed by the methods known to the skilled man. Preferable methods are e.g. the organic solvent immersion, the incipient wetness impregnation or the melt methods. Said methods are disclosed e.g. in Limnell et al., "Drug Delivery Formulations of Ordered and Nonordered Mesoporous Silica: Comparison of Three Drug Loading Methods", J. Pharm. Sc. Vol. 100 (8) (2011) and in Mellaerts et al. "Physical state of poorly water soluble therapeutic molecules loaded into SBA-15 ordered mesoporous silica carriers: A case study with itraconazole and ibuprofen", Langmuir 24:8651-8659(2008), which are incorporated herein with regard to loading of mesoporous materials.

Typically, the active ingredient is dissolved in an appropriate solvent to provide a solution which is then applied onto the mesoporous material. Generally, the amount of loaded active ingredient is expressed in weight percentage based on the total weight of the amount of mesoporous material and the active ingredient. Mesoporous materials may be loaded with up to 60% wt of active ingredient(s). Typically, the mesoporous particles are loaded with about 30% wt of the active ingredient(s).

Of the various types of polymer solid dispersions available in the art, three are typically encountered in pharmaceutical applications. The drug can be dissolved, dispersed in an amorphous state or dispersed in a crystalline state. Thermodynamically stable formulations are achieved when the drug is either completely dissolved below its saturation solubility in the polymer or it is dispersed in a crystalline form. When the active ingredient is dissolved below its saturation solubility, it results in a solid solution. When the drug concentration exceeds its saturation solubility, the drug may crystallize or precipitate out of the polymer during storage, hence changing its dissolution and biopharmaceutical properties. When the active ingredient is in a crystalline form, the system remains quite stable.

Solid dispersion techniques are known and applied as such to enhance the dissolution of poorly soluble drugs as an alternative to the micronization or the use of surfactants. However, solid dispersions have not been disclosed as a covering or coating material for loaded mesoporous particles.

The term "polymer solid dispersion" as used herein particularly means the dispersion of the amorphous or dissolved active pharmaceutical ingredient(s) in an inert carrier matrix, preferably prepared by the melting of a polymer. Both dispersion types show dissolution advantages, although the amorphous solid dispersions are usually considered as thermodynamically unstable.

Without being bound by any theory, the applicant believes that the active ingredient on the external surface of the mesoporous material may re-crystallize due to the available space outside the pores. Such phenomenon not only prevents the dissolution of the active ingredient deposited on the external surface of the mesoporous material, which thus limits the loading capacity of the final dosage form, but it also blocks the pores and entraps the active ingredient contained inside the pores, which substantially impacts the dissolution of the loaded active ingredient.

It is furthermore believed that the polymer solid dispersion according to the present invention does not enter into the pores of the mesoporous particles, as a polymer in an organic or an aqueous solution could do, and would therefore prevent the desorption of the active ingredient already loaded inside the structure of the carrier.

The dosage forms according to the present invention overcome the above cited problems by converting substantially all the crystalline particles of the active ingredient on the external surface of the mesoporous particles in an amorphous or molecularly dispersed and soluble form, while ensuring the dissolution of the drug loaded in the pores of the mesoporous carrier. Typically, the dosage forms according to the present invention comprise less than 5% wt, preferably less than 1% wt of crystalline forms of the active ingredient(s). More preferably, the dosage forms according to the present invention are free of crystalline forms of the active ingredient(s).

It has also been unexpectedly found that the polymer solid dispersion on the external surface of the mesoporous particles can further increase the dissolution rate of the active pharmaceutical ingredient as a whole in comparison to the dissolution of loaded mesoporous materials without a polymer solid dispersion.

The solid dispersion according to the present invention may comprise one or more polymers selected from the group of cellulose derivatives, polyacrylates, polyvinyl derivatives, polyalkylene oxides, polyamino saccharides, and mixtures thereof. A derivative of a polymer in this regard thereby relates to a compound that is derived from the original polymer, e.g. in case of a cellulose derivative from cellulose, by any derivatization reaction, thus leading to a product with similar chemical structure.

Examples of said polymers may be alkyl cellulose (e.g., methyl cellulose and ethyl cellulose), cellulose acetate phthalate (CAP), hydroxyalkyl cellulose (e.g., hydroxymethyl cellulose, hydroxyethyl cellulose, hydroxypropyl cellulose, and hydroxybutyl cellulose), hydroxyalkylalkyl cellulose (e.g., hydroxyethylmethyl cellulose and hydroxypropylmethyl cellulose (HPMC) hydroxyalkylalkyl cellulose ester (e.g., hydroxypropylmethyl cellulose phthalate (HPMCP)), hydroxypropylmethyl cellulose acetate succinate (HPMCAS), carboxyalkyl cellulose (e.g., carboxymethyl cellulose and alkali metal salts thereof, such as sodium salts), carboxyalkylalkyl cellulose (e.g., carboxymethylethyl cellulose), carboxyalkyl cellulose ester (e.g., carboxymethyl cellulose butyrate, carboxymethyl cellulose propionate, carboxymethyl cellulose acetate butyrate, carboxymethyl cellulose acetate propionate, poly(methacylic acid-co-methyl methacrylate 1:2), poly(methacrylic acid-co-methyl methacrylate 1:1), Poly(methyl acrylate-co-methyl methacrylate-co-methacrylic acid 7:3:1), poly(butyl methacrylate-co-(2-dimethylaminoethyl) methacrylate-co-methyl methacrylate 1:2:1), poly(ethyl acrylate-co-methyl methacrylate 2:1), poly(ethyl acrylate-co-methyl methacrylate 2:1), poly(ethyl acrylate-co-methyl methacrylate-co-trimethylammonioethyl methacrylate chloride 1:2:0.2), poly(ethyl acrylate-co-methyl methacrylate-co-trimethylammonioethyl methacrylate chloride 1:2:0.1), polyvinyl pyrrolidone, polyvinyl acetate, copolymer of polyvinyl pyrrolidone and polyvinyl acetate, polyvinyl caprolactam-polyvinyl acetate-PEG graft copolymer, polyvinyl alcohol/acrylic acid/methyl methacrylate copolymer, polyalkylene oxide, chitosan, chitin and copolymers and mixtures thereof.

Preferably, the solid dispersion is prepared by using cellulose derivatives, polyvinyl derivatives, polyacrylates and copolymers and mixtures thereof.

The skilled person is able to select the suitable polymer(s) for solubilizing or dispersing the active ingredient(s) in an amorphous form in a final solid dispersion. Regarding rivaroxaban, suitable polymers for preparing a polymer solid dispersion of rivaroxaban are e.g. polyvinylpyrrolidone, polyvinyl caprolactam-polyvinyl acetate-PEG graft copolymer, hydroxypropyl cellulose, polyethylenglycol, polymethacrylate, polymethylmethacrylate, polyethylenoxide, polyoxyethylene polyoxypropylen block copolymer, vinylpyrrolidone vinylacetate copolymer, or mixtures thereof.

In the conventional hot melt solid dispersions substantial amounts of polymers are required to dissolve the total amount of active pharmaceutical ingredient(s). Thus, in order to limit the size of the final dosage forms, the trend is to approach the saturation concentration of the polymer, which usually leads to stability problems of the composition and renders the behavior of the solid dispersion unpredictable.

The present invention solves the above problems by using a polymer to cover the external surface of the mesoporous particles, allowing the polymer to dissolve the crystalline active pharmaceutical ingredient on the external surface of the mesoporous particles or disperse other forms of the active pharmaceutical ingredient. The amount of the crystalline active pharmaceutical ingredient on the external surface of the mesoporous particles is only a part of the whole amount of the active pharmaceutical ingredient. The dosage forms according to the present invention thus require lower amounts of the polymer(s) than the dosage forms of the prior art. The dosage forms according to the present invention do not impact the size of the final forms while ensuring the stability of the active pharmaceutical ingredient contained therein. The dosage forms according to the present invention can thus increase the loading capability of said dosage forms.

Further described is a process of a preparation of a pharmaceutical dosage form of a poorly soluble active ingredient, preferably a poorly soluble active pharmaceutical ingredient, which comprises the preparation of a solid dispersion of at least one polymer with a mesoporous material loaded with said active ingredient.

Another aspect of the present invention is directed to the process of a preparation of a pharmaceutical dosage form of a poorly soluble active pharmaceutical ingredient which comprises loading the poorly soluble active pharmaceutical ingredient onto and into a mesoporous material, and dispersing the mesoporous material loaded with the active pharmaceutical ingredient with at least one polymer to prepare a solid dispersion of at least one polymer with a mesoporous material loaded with said active pharmaceutical ingredient.

The active pharmaceutical ingredient is loaded into and onto the mesoporous material using methods known in the art, e.g. the solvent immersion, the incipient wetness impregnation or the melt method. After the loading, the remaining solvent is removed from the system by the methods known in the art, e.g. by drying processes. Suitable methods to remove the solvents are disclosed e.g. in WO 9833485, which is incorporated herein with regard to solvent removal.

Suitable solvents for dissolving a poorly soluble drug and achieving a substantial loading of the drug are known to the man skilled in the art. Preferably, the solvent is selected from the solvents disclosed in ICH Harmonized Tripartite Guideline; Impurities: Guideline for Residual Solvents Q3C (R5), current Step 4 version; 4 Feb. 2011. Suitable solvents may be e.g. acetic acid, acetone, acetonitrile, anisole, 1-butanol, 2-butanol, butyl acetate, tert-Butylmethyl ether, cumene, dimethyl sulfoxide (DMSO), dimethyl formamide (DMF), ethanol, ethyl acetate, ethyl ether, ethyl formate, formic acid, heptane, isobutyl acetate, isopropyl acetate, methyl acetate, 3-methyl-1-butanol, methylethylketone, methylisobutylketone, 2-methyl-1-propanol, pentane, 1-pentanol, 1-propanol, 2-propanol, propyl acetate, and mixtures thereof.

Suitable solvents for rivaroxaban may be e.g. acetic acid, acetone, DMSO, DMF, ethanol and mixtures thereof.

Preferably, the amount of rivaroxaban loaded in the mesoporous particles is in the range of 10 to 50% wt and more preferably in the range of 20 to 40% wt.

Techniques are known in the prior art to prepare solid dispersions. Preferably, the loaded mesoporous material can be subjected to a hot melt granulation or a hot melt extrusion with the appropriate polymer(s). Particularly preferred is the hot melt extrusion which enables a homogeneous covering, e.g. coating, of the mesoporous particles with the melted polymer. Appropriate apparatus are available in the art from e.g. Breitenbach, J., "Melt extrusion: From process to drug delivery technology", European Journal of Pharmaceutics and Biopharmaceutics 54 (2002), 107-117, which is incorporated herein with regard to melt extrusion.

According to the present invention, the total amount of polymer(s) used in the melting process can be lower in comparison to the amount of mesoporous material.

The weight ratio between the polymer and the mesoporous material is preferably between 1:3 to 3:1, more preferably in the range of 1:2 to 2:1 and most preferably in the range of 2:3 to 3:2.

Furthermore, the total amount of polymers used in the melting process according to the present invention is lower in comparison to the typical hot melt extrusion. The weight ratio between the active pharmaceutical ingredient and the polymer is preferably between 1:10 to 2:1, more preferably in the range of 1:6 to 1.5:1 and most preferably in the range of 2:5 to 1:1.

Advantageously, the hot melt composition may further comprise a filler to improve the tackiness of the texture of the resulting product, making it easier to handle. Suitable fillers are e.g. non-mesoporous silica, talcum, magnesium stearate or mixtures thereof. Such fillers are particularly useful for the hot melt extrusion. The hot melt composition may further comprise a plasticizer. Suitable plasticizers are e.g. polyalkylene oxide, glycerin, polyethylene glycols, polyethylene glycol monomethyl ether, d-α-tocopheryl PEG 1000 succinate, macrogol glycerol hydroxystearate, poloxamers, propylene glycol, sorbitol sorbitan solution, acetyl tributyl citrate, acetyl triethyl citrate, castor oil, diacetylated monoglycerides, dibutyl sebacate, diethyl phthalate, triacetin, tributyl citrate, triethyl citrate and mixtures thereof.

Finally, the resulting melt or extrudates are collected, optionally milled and formulated into pharmaceutical dosage forms. The pharmaceutical dosage forms may optionally contain further pharmaceutical excipients known to the man skilled in the art.

Suitable excipients are known in the art and disclosed e.g. in "Handbook of Pharmaceutical excipients", 2nd Ed. 25 1994, American Pharmaceutical Association, Washington, Wade A., Weller P J and in Rowe et al., "Handbook of Pharmaceutical Excipients", 7th Ed., London: Pharmaceutical Press, 2012, which are incorporated herein with regard to excipients.

Examples of suitable pharmaceutical dosage forms are tablets, microtablets, sachets, slugs, capsules, granulates or compressed granulates. Preferable dosage forms are tablets or capsules.

EXAMPLES

Example 1: Loading of Ibuprofen Into Mesoporous Materials

The loading of 40% wt ibuprofen, a typical example of a poorly soluble drug, was performed in a single-pot system (Mini-Turbo-Wave, Pro CepT).

Before the loading process, the filter temperature was pre-heated to 60° C., the cover temperature to 45° C. and the condenser cooled down to 5° C. 300 ml of mesoporous silica (Syloid AL-1 FP having a pore diameter of 3.2 nm) was filled into the bowl. Once the system was closed, the system was inertized three times ensuring the oxygen replacement by nitrogen.

The incipient wetness impregnation method was used to load the ibuprofen into the mesoporous silica. A nitrogen flow of 30 ml min$^{-1}$ was maintained during the whole process. 40% of ibuprofen (by weight based on the total amount of active ingredient and the carrier) was dissolved in a volume of absolute ethanol of about 4 times that of the silica pore volume, i.e. a volume of 160 ml, resulting in a solution "S".

The solution "S" was added dropwise to the mesoporous silica through a peristaltic pump. The speed of the impeller was set to 50 rpm during the impregnation process. After addition of the solution, the suspension was stirred for another 10 min at 100 rpm before drying.

The drying was performed by convection with hot air under vacuum at 150 mbar, 70° C. and under stirring at 100 rpm to ensure fast evaporation of the ethanol. The drying process was stopped once no more ethanol condensation was observed. Powder sample was collected and put in a vacuum oven for additional drying for 24 h (T=40° C.)

DSC was performed in order to assess the physical state of the drug compound. Silica sample (4-8 mg) was heated from 25° C. to 150° C. using a heating rate of 10° C. min$^{-1}$. All experiments were performed in 40 μl closed aluminium pans. Samples were analyzed in triplicate.

Figure 1:
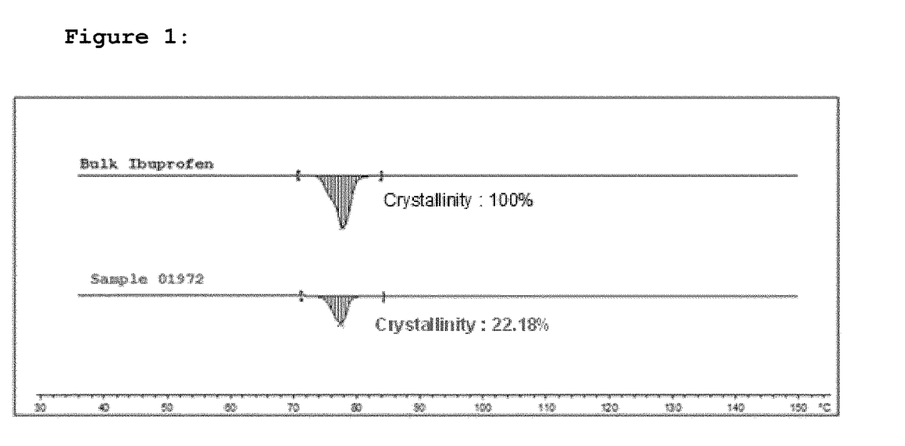
FIG. 1 illustrates the DSC (differential scanning calorimetry) analysis of the silica samples prepared and loaded (40% wt) with ibuprofen as disclosed in example 1 and of bulk ibuprofen.

The results are illustrated in FIG. 1. The DSC analysis shows a melting peak for the ibuprofen adsorbed on Syloid AL-1 FP showing that a crystalline fraction was present. As the peak is sharp and the melting temperature is not depressed, this crystalline part is exclusively located on the external surface of the silica. This fraction represents 22.18% of the ibuprofen load.

Example 2: Loading of Rivaroxaban Into Mesoporous Materials

The same process as described in example 1 was applied to another poorly soluble drug rivaroxaban. The process was performed in the single-pot system to incorporate 20% wt of rivaroxaban into Syloid 72FP (having a pore diameter of 10.0 nm).

The solution "S" was prepared by dissolving rivaroxaban in a DMSO/acetone mixture (DMSO:acetone 2:8 by volume) in a volume of about 6 times of the pore volume of the mesoporous material.

The solution "S" was added dropwise to the Syloid 72 FP material through a peristaltic pump. The impeller was set to 50 rpm during the impregnation process.

Powder sample was collected and put in a vacuum oven for additional drying for 24 h (T=40° C.)

Similarly as in example 1, DSC measures were performed. Each sample was heated from 30° C. to 270° C. using a heating rate of 10° C. min$^{-1}$.

Figure 2:
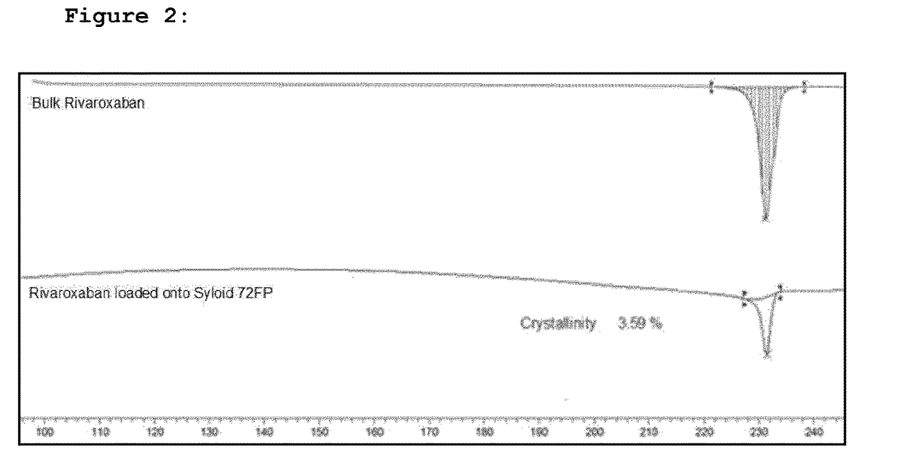
FIG. 2 illustrates the DSC analysis of the silica samples prepared and loaded (20% wt) with rivaroxaban as disclosed in example 2 and of bulk rivaroxaban.

The results, illustrated in FIG. 2, clearly show that the reference crystalline rivaroxaban exhibits an endothermic peak at 231.4° C. and a melting enthalpy of 110.4 J.g$^{-1}$, whereas the rivaroxaban loaded in Syloid 72FP exhibits a crystalline fraction of 3.6%. Similar approaches may be conducted for sample loaded with different, e.g. 40% wt of rivaroxaban.

Example 3: Hot Melt Extrudates of Loaded Mesoporous Silica

A sample of silica (Syloid Al-1 FP) loaded with 40% wt ibuprofen ("IBU") prepared according to example 1 (sample 01972) was extruded together with Eudragit® E PO polymer (Poly(butyl methacrylate-co-(2-dimethylaminoethyl) methacrylate-co-methyl methacrylate) 1:2:1; Evonik). The hot melt extrusion ("HME") compositions are illustrated in table 1.

TABLE 1

| | IBU loaded in silica before hot-melt extrusion | Mixture composition (IBU/Syloid Al-1 FP/Eudragit ® E PO) | Total API/ Polymer Ratio | External API/ Polymer Ratio |
|---|---|---|---|---|
| Sample 01972, loaded with 40% wt IBU | 17.8 wt. % amorphous or molecularly dispersed IBU inside pores 22.2 wt. % crystalline IBU outside pores | 29.0/43.3/27.7 (based on 100 wt. % of the whole composition) | 1.04 | 0.6 |

22.2 wt. % of the 40% wt drug load was accumulated outside the pores as crystalline ibuprofen. The other 17.8 wt. % of ibuprofen was amorphous or molecularly dispersed inside the silica pores.

Hot-melt extrusion (HME) was carried out using twin-screw extruder (ZE9, Three-Tec). Screws were co-rotated at a speed of approximately 200 rpm. The applied temperature consisted of a temperature ramp between 40° C. to 120° C. (Z1=40° C., Z2=50° C., Z3=60° C., Z4=70° C., Z5=80° C., Z6=80° C., Z7=120° C. and Z8=120° C.). The extrudates were collected and milled.

Figure 3:
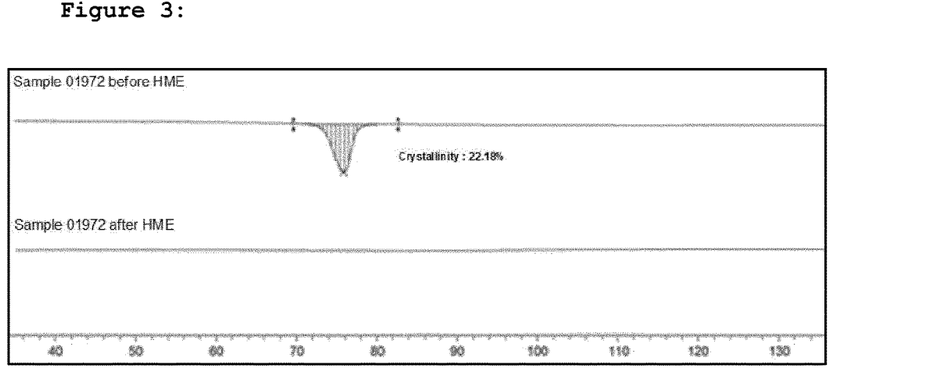
FIG. 3 illustrates the DSC analysis of the samples of example 3 (silica loaded with ibuprofen) measured before and after hot melt extrusion (HME).

The batches were subjected to DSC before and after the hot melt extrusion. The results, illustrated in FIG. 3, show that the dissolution of ibuprofen in the polymer (Eudragit® E PO) occurred. There is no measurable melting point in the sample after HME, which evidences that the polymer was able to convert the crystalline part loaded on the external surface of the silica material into an amorphous or molecularly dispersed form.

One can notice that there was only the external crystalline ibuprofen which had to be converted (External API/Polymer Ratio:0.6).

One can further notice that this formulation (without any crystal) contained more API than polymer (Total API/Polymer Ratio>1), which is extremely high compared to the ratio obtained from typical polymer solid dispersions (ratio≤0.6).

In order to simulate the behaviour of the tested materials after oral administration, a dissolution test was conducted over 120 min in an acidic medium (pH 1.0) and then in a pH 7.2 buffer. The dissolution profile of ibuprofen was measured using a USP 2 dissolution tester with an online flow cell UV-vis analysis system. The in vitro release studies were carried out in 700 ml of degassed 0.1 M HCl equilibrated to a temperature of 37° C. and was placed in the vessel (acid stage). 20 mg of pure ibuprofen crystals and the corresponding amount of 20 mg ibuprofen from the loaded silica samples were used for the dissolution testing.

After 1 h of operation in 0.1 M HCl, the dissolution medium was completed by adding to the HCl 300 ml of degassed 0.2 M trisodium phosphate dodecahydrate buffer equilibrated to 37° C. and adjusted to a pH of 7.2 with 1 M sodium hydroxide (buffer stage). The stirring rate in the acid stage was 100 rpm and in the buffer stage it was 150 rpm. Samples were taken by auto sampling system equipped with filters respectively at intervals of 5 min and 10 min. After each measurement, the liquid samples were conveyed back to the dissolution vessels by a peristaltic pump. UV measurements were taken at a wavelength of 222 nm (reference wavelength 400 nm).

Figure 4:
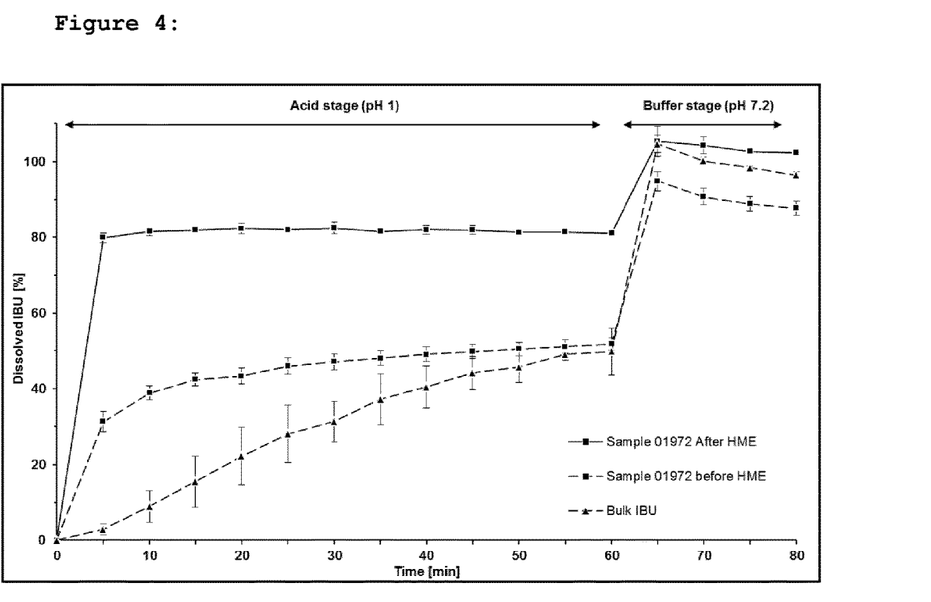
FIG. 4 illustrates the pH dependent dissolution profiles of the samples prepared in example 3 (bulk ibuprofen, silica loaded with ibuprofen and silica loaded with ibuprofen after HME).

The dissolution profiles of the samples (01972) before and after hot melt extrusion were obtained. The results are illustrated in FIG. 4.

One can see that the dissolution of the loaded silica sample is faster than the dissolution of pure ibuprofen crystals. However, the dissolution of the loaded silica sample is slower due to the crystalline part on the external surfaces of the mesoporous particles compared to the dissolution of the hot melt extruded sample.

Example 4: Hot Melt Extrudate of Rivaroxaban Loaded Mesoporous Neusilin®

A sample of mesoporous magnesium alumino-metasilicate loaded with rivaroxaban (RIVA) was prepared according to the process described in example 2.

Neusilin® US2 (2.69 g) was loaded with 24 wt. % (0.83 g) of Rivaroxaban and DSC measures were performed using the same protocol as described in example 2.

Figure 5:
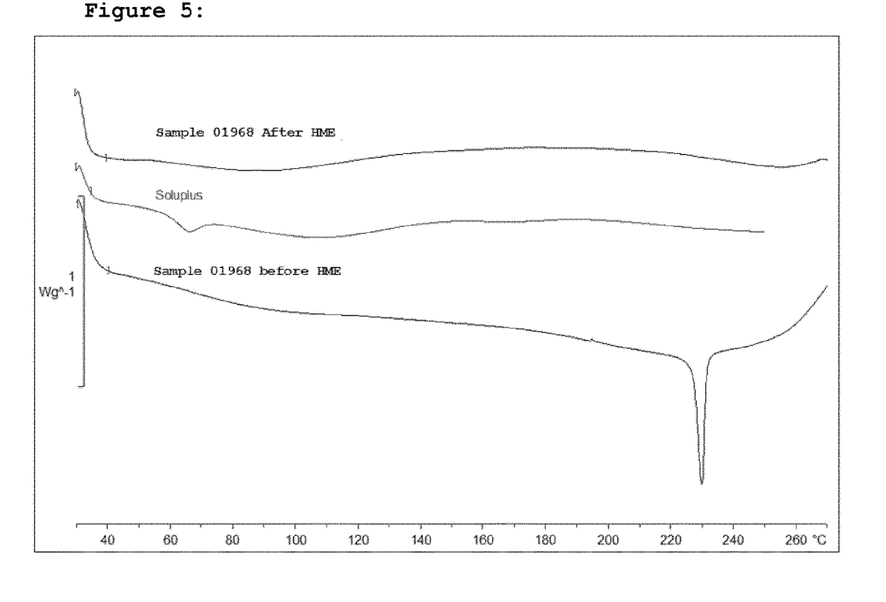
FIG. 5 illustrates the DSC analyses of the mesoporous magnesium alumino-metasilicate samples loaded (24%) with rivaroxaban measured before and after hot melt extrusion of Example 4.

The results present a sharp endothermic peak at 231° C., showing crystals on the external surface of the Neusilin®, as can be seen in FIG. 5, bottom line. According to the melting enthalpy of pure rivaroxaban, one can see that 45.61% of the loaded API are crystalline outside of the pores, and 54.39% are amorphous or molecularly dispersed, as shown in table 2, left column regarding bulk RIVA or RIVA loaded in silica.

As first trials showed that it was not possible to dissolve more than 10% of rivaroxaban into Soluplus® (total API/Polymer ratio=0.1), this limit was set.

The loaded sample was extruded together with Soluplus® polymer (polyvinyl caprolactam-polyvinyl acetate-polyethylene glycol graft copolymer; BASF) (8.00 g) and with pure rivaroxaban (0.42 g). The amount of the bulk crystalline API (active pharmaceutical ingredient) added was calculated in order to saturate the polymer. (External crystalline loaded API+External bulk crystalline API represent 10% of Soluplus (w/w): (External API/Polymer ratio=0.1).

The mixture composition is shown in the right three columns of Table 2:

TABLE 2

| | RIVA loaded in silica before hot-melt extrusion | Mixture composition (Riva/Neusilin ®US2/ Soluplus ®) | Total API/ Polymer Ratio | External API/ Polymer Ratio |
|---|---|---|---|---|
| Sample 01968, loaded with 24% wt Rivaroxaban | 13.1 wt. % amorphous or molecularly dispersed RIVA inside pores 10.9 wt. % crystalline RIVA outside pores | 10.5/22.5/67 (based on 100 wt. % of the whole composition) | 0.16 | 0.1 |

Hot-melt extrusion (HME) was carried out using twin-screw extruder (ZE9, Three-Tec). Screws were co-rotated at a speed of approximately 100 rpm. The applied temperature consisted of a temperature ramp between 50° C. to 180° C. (Z1=50° C., Z2=100° C., Z3=130° C., Z4=160° C., Z5=180° C., Z6=180° C., Z7=180° C. and Z8=180° C.). The extrudates were collected and milled.

The batches were subjected to DSC before and after the hot melt extrusion, the results of which are seen in FIG. 5. For comparison, a curve of pure Soluplus® was also recorded. There is no measurable melting point in the sample after HME. This shows that the polymer was able to convert the crystalline part loaded onto the external surface of the carrier, and also the bulk API into an amorphous or molecularly dispersed form.

As the concentration of the external API in the polymer was at the saturation point, this also shows that the loaded amorphous or molecularly dispersed part was not altered and that the polymer did not enter in the mesoporous structure.

One can further notice that a higher amount of the loaded Neusilin® will show a higher amount of external crystalline API. This concentration can be fixed at the saturation level of the polymer. This will lead to a substantial higher concentration of API, more than the double of the saturation point, as the internal amorphous or molecularly dispersed loaded part represents 54.39% of loaded Neusilin®.

In order to simulate the behaviour of the tested materials after oral administration, a dissolution test was conducted over 60 min in an acidic medium (pH 4.5). The marketed reference Xarelto® 20 mg, 20 mg of pure Rivaroxaban crystals and the corresponding amount of 20 mg Rivaroxaban from the samples were used for the dissolution testing. This corresponds to non-sink conditions, allowing investigation of the supersaturation (increase in solubility).

The dissolution profile of Rivaroxaban was measured using a USP 2 dissolution tester with an online flow cell UV-vis analysis system.

The in vitro release studies were carried out in 900 ml degassed acetate buffer pH 4.5, which was put into each vessel, and equilibrated to 37° C. The stirring was set to 75 rpm. Samples were taken using the auto sampler. For each batch the dissolution profiles of 3 samples were taken and the mean value is presented in FIG. 6.

Figure 6:
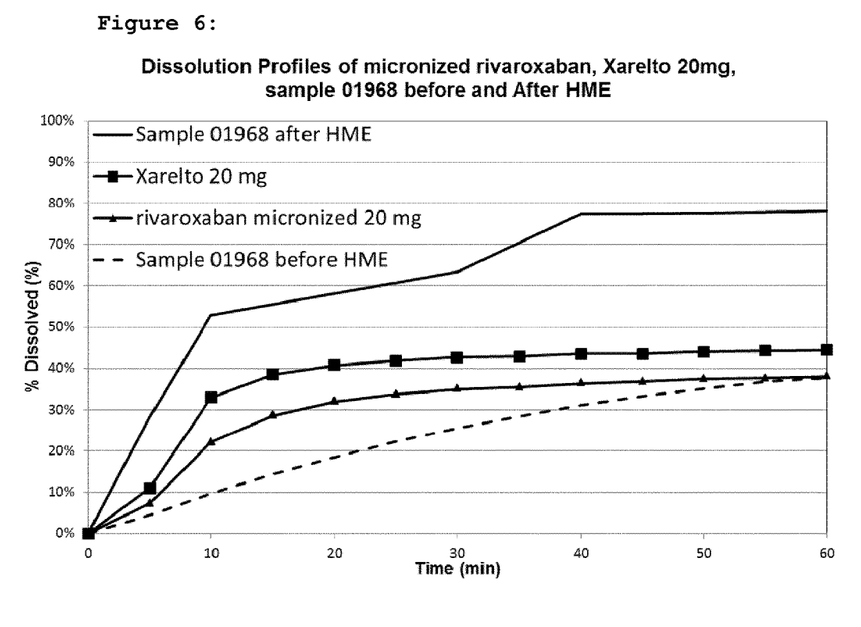
FIG. 6 illustrates the dissolution profiles of bulk micronized rivaroxaban, marketed reference Xarelto® 20 mg and the samples prepared in example 4: mesoporous carrier loaded with rivaroxaban and mesoporous carrier loaded with rivaroxaban after HME.

One can see that the dissolution of the loaded silica sample is quite comparable, even slower than the dissolution of pure rivaroxaban microcrystals, which is mainly due to the crystalline part on the external surface of the mesoporous carrier.

However, it is obvious that the hot melt extruded samples display an increased solubility (supersaturation) compared to the loaded silica samples without thermic treatment. The solubility is increased by a factor of 2.1 after 60 minutes.

This is in line with the DSC results showing that there is no more crystals on the surface of the mesoporous loaded sample after the hot melt operation.

The invention claimed is:

1. A pharmaceutical dosage form comprising particles of a mesoporous material loaded with a poorly soluble active pharmaceutical ingredient,
   wherein the mesoporous material is a silica based material,
   wherein external surfaces of the particles of the mesoporous material are at least partially covered with a polymer solid dispersion of the poorly soluble active pharmaceutical ingredient and
   wherein the pores of the mesoporous material are also loaded with the poorly soluble active pharmaceutical ingredient,
   wherein the poorly soluble active pharmaceutical ingredient is rivaroxaban.

2. The pharmaceutical dosage form according to claim 1, wherein the polymer solid dispersion of the poorly soluble active pharmaceutical ingredient is an amorphous solid dispersion or a solid solution.

3. The pharmaceutical dosage form according to claim 1, wherein the external surfaces of the particles of the mesoporous material are covered with the polymer solid dispersion.

4. The pharmaceutical dosage form according to claim 1, wherein the mesoporous material has a pore size in the range of 2 to 50 nm.

5. The pharmaceutical dosage form according to claim 1, wherein the amount of the poorly soluble active pharmaceutical ingredient is between 5 and 60% wt of the total weight of the mesoporous material and the poorly soluble active pharmaceutical ingredient.

6. The pharmaceutical dosage form according to claim 1, wherein the pharmaceutical dosage form comprises less than 5% wt of the poorly soluble active pharmaceutical ingredient in a crystalline form.

7. The pharmaceutical dosage form according to claim 1, wherein the pharmaceutical dosage form is in the form of a tablet or a capsule.

8. The pharmaceutical dosage form according to claim 1, wherein the poorly soluble active pharmaceutical ingredient is rivaroxaban in an amount of 10, 15 or 20 mg.

9. A process for the preparation of the pharmaceutical dosage form of claim 1 comprising particles of a mesoporous material loaded with a poorly soluble active pharmaceutical ingredient, wherein the poorly soluble active pharmaceutical ingredient is rivaroxaban and the mesoporous material is a silica based material, the process comprising the steps of:
   loading the rivaroxaban onto and into a mesoporous material, and
   dispersing the mesoporous material loaded with the rivaroxaban with at least one polymer to prepare a polymer solid dispersion of at least one polymer with the particles of mesoporous material loaded with rivaroxaban.

10. The process according to claim 9, wherein the particles of the mesoporous material are at least partially covered with the polymer solid dispersion.

11. The process according to claim 9, wherein the polymer solid dispersion is prepared by hot melt extrusion or by hot melt granulation of the at least one polymer and the mesoporous material loaded with the poorly soluble active pharmaceutical ingredient.

12. The pharmaceutical dosage of claim 1, wherein substantially all of the poorly soluble active pharmaceutical ingredient on the external surfaces of the particles of the mesoporous material is in amorphous or molecularly dispersed and soluble form.

* * * * *